(12) United States Patent
Takahashi et al.

(10) Patent No.: US 10,806,564 B2
(45) Date of Patent: Oct. 20, 2020

(54) CATHETER SYSTEMS AND METHODS OF TREATING A VASCULAR DISEASE USING THE SAME

(71) Applicant: Asahi Kasei Kabushiki Kaisha, Tokyo (JP)

(72) Inventors: Tetsuko Takahashi, Nobeoka (JP); Akihito Nakazawa, Moriyama (JP); Keiichi Toyoda, Nobeoka (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 148 days.

(21) Appl. No.: 16/110,426

(22) Filed: Aug. 23, 2018

(65) Prior Publication Data

US 2019/0060053 A1    Feb. 28, 2019

Related U.S. Application Data

(60) Provisional application No. 62/549,108, filed on Aug. 23, 2017.

(51) Int. Cl.

| | | |
|---|---|---|
| *A61F 2/07* | (2013.01) | |
| *A61F 2/95* | (2013.01) | |
| *A61M 25/09* | (2006.01) | |
| *A61F 2/958* | (2013.01) | |
| *A61F 2/89* | (2013.01) | |
| *A61M 25/00* | (2006.01) | |
| *A61B 5/02* | (2006.01) | |

(52) U.S. Cl.
CPC ............... *A61F 2/07* (2013.01); *A61M 25/09* (2013.01); *A61B 5/02014* (2013.01); *A61F 2/89* (2013.01); *A61F 2/958* (2013.01); *A61F 2002/075* (2013.01); *A61F 2250/0039* (2013.01); *A61M 25/0068* (2013.01)

(58) Field of Classification Search
CPC ................. A61F 2/07; A61F 2/82; A61F 2/95
USPC .................................................. 623/1.1–1.36
See application file for complete search history.

(56) References Cited

U.S. PATENT DOCUMENTS

| | | | |
|---|---|---|---|
| 10,383,750 B1 * | 8/2019 | Sirhan .................... | A61F 2/915 |
| 2012/0055614 A1 * | 3/2012 | Hancock ............ | A61B 17/12022 |
| | | | 156/172 |
| 2012/0070600 A1 * | 3/2012 | Muratoglu .............. | A61L 27/16 |
| | | | 428/36.92 |
| 2014/0100649 A1 * | 4/2014 | Gada ....................... | A61L 31/06 |
| | | | 623/1.16 |
| 2014/0188208 A1 * | 7/2014 | Hancock ............ | A61B 17/12022 |
| | | | 623/1.11 |
| 2017/0290686 A1 * | 10/2017 | Sirhan ....................... | A61F 2/90 |
| 2018/0161184 A1 * | 6/2018 | Laduca ..................... | A61F 2/90 |
| 2018/0263753 A1 * | 9/2018 | Vinluan .................... | A61F 2/07 |
| 2018/0318113 A1 * | 11/2018 | Sirhan .................... | A61F 2/915 |
| 2019/0231564 A1 * | 8/2019 | Sirhan ...................... | A61F 2/90 |
| 2019/0365548 A1 * | 12/2019 | Sirhan .................... | A61F 2/915 |

* cited by examiner

*Primary Examiner* — Suzette J Gherbi
(74) *Attorney, Agent, or Firm* — Morgan, Lewis & Bockius LLP

(57) ABSTRACT

The present invention relates to catheter systems and methods of treating a vascular disease using the same.

28 Claims, No Drawings

CATHETER SYSTEMS AND METHODS OF TREATING A VASCULAR DISEASE USING THE SAME

BACKGROUND OF THE INVENTION

Field of the Invention

The present invention relates to catheter systems and methods of treating a vascular disease using the same.

Description of the Related Art

Stent grafts are medical devices for use in the treatment of vascular diseases. For example, stent grafts have been used to treat thoracic or abdominal aortic aneurysm and are in the form of an artificial blood vessel fitted with a tubular fabric, for example, in a spring-like material known as a stent. The intravascular treatment of aortic aneurysm using the stent graft is, for example, a method of treatment in which: the artery at the base of the foot is incised; a catheter having the stent graft compressively inserted therein (stent graft device) is introduced through the incision and transferred to the affected area of aneurysm using a guide wire; and the stent graft is opened from the catheter and indwelled at the affected area, whereby blood flow into the aneurysm is blocked and burst of the aneurysm is prevented. Unlike artificial blood vessel replacement, which is a conventional method for treating aortic aneurysm, this treatment method does not involve thoracotomy or laparotomy. Therefore, in recent years, its application has been rapidly increasing because physical burdens or economic burdens ascribable to long-term hospitalization on patients are reduced.

However, most of the currently commercially available stent graft devices have a catheter outer diameter exceeding 18 Fr (French) (3 Fr is about 1 mm; thus 18 Fr corresponds to a diameter of about 6 mm). In many cases, females and Asians have less than 6 mm diameters of iliac arteries serving as routes for catheterization. Also, aneurysm patients may have preexisting conditions, such as diabetes mellitus, and their blood vessels are often fragile and calcified. Therefore, the risk of vascular damage is increased during access to the affected areas even if the diameters of blood vessels are larger than the diameters of catheters.

The present disclosure provides catheter systems using very thin grafts and suppressing type III endoleak. The present disclosure also provides methods of treating a vascular disease in a subject in need thereof using the catheter systems.

SUMMARY OF THE INVENTION

The disclosure is related to a method of treating a vascular disease in a subject in need thereof, comprising: inserting a catheter system into a blood vessel of the subject, wherein the catheter system comprises a catheter and a stent graft comprising a stent and a graft; delivering the catheter system to an area of interest in the blood vessel; and expanding the stent graft in the blood vessel, wherein compressed volume/expanded volume of the stent graft is 2.5% or less.

In some embodiments, from 85 to 65% of the total inner cavity of the catheter inserted into the blood vessel is void.

In some embodiments, the vascular disease is aortic aneurysm, and the area of interest is an area of aneurysm. In additional embodiments, the vascular disease is selected from the group consisting of abdominal aortic aneurysm and thoracic aortic aneurysm. In further embodiments, the catheter is 15 French (Fr) or less, and the vascular disease is abdominal aortic aneurysm. In yet further embodiments, the catheter is 18 Fr or less, and the vascular disease is a thoracic aortic aneurysm.

In some embodiments, the stent and the graft are stitched with a suture thread. In additional embodiments, the stent comprises at least one material selected from the group consisting of shape memory alloys, superelastic metals or synthetic polymer materials.

In some embodiments, the graft has a flexural rigidity of not more than 0.050 gf·cm$^2$/cm measured by Kawabata evaluation system (KES). In additional embodiments, the graft has a thickness of from 10 to 90 µm. In yet additional embodiments, the graft comprises at least 20 wt % of a polyester fiber. In further embodiments, the graft comprises a polyester fiber having 98 wt % or greater polyethylene terephthalate component and satisfying the following conditions: (1) a reduced viscosity ($\eta sp/c$) of 0.80 dl/g or greater, (2) a total fineness of between 7 dtex and 120 dtex, inclusive, and a single filament fineness of 0.5 dtex or less, and (3) a toughness parameter X of 2.0 or greater as represented by the following formula: X=(tensile strength× tensile elongation)/(total fineness×single filament fineness); a tensile strength of 3.5 cN/dtex or greater; and a tensile elongation of 12% or greater. In yet further embodiments, the polyester fiber further satisfies the following conditions: (4) for each of 10 sampled fiber bundles, where 10 fiber bundles of 1 cm are sampled at equal spacing of 3 m in the yarn length direction, the interfilament variation $Y_{(1-10)}$ represented by the following formula is 0.5 or less:

$$Y_{(1-10)} = \sqrt{\{(d_i - d_{av})^2/(n-1)\}}$$

wherein n is a number of filaments corresponding to at least 30% of the total number of filaments from each of 10 fiber bundles, the yarn diameter $d_i$ is the diameter of each yarn among n filaments corresponding to at least 30% of the total number of filaments from each of 10 fiber bundles, and $d_{av}$ is the average for n filaments. In some embodiments, the graft is tubular and/or branched.

In some embodiments, the subject is Asian. In additional embodiments, the subject has diabetes mellitus.

The disclosure is also related to a catheter system comprising the catheter and the stent graft described herein in which the stent graft comprises the graft and the stent that are connected with a suture, wherein a compression ratio of the stent graft is 2.5% or less, and a filling factor of the stent graft in the catheter is 25 to 35%.

DETAILED DESCRIPTION OF THE EMBODIMENTS

The following detailed description is directed to certain specific embodiments of the invention. However, the invention can be embodied in a multitude of different ways. In this description, reference is made to the drawing wherein like parts are designated with like numerals throughout.

The disclosure is related to a method of treating a vascular disease in a subject in need thereof, comprising: inserting a catheter system into a blood vessel of the subject, wherein the catheter system comprises a catheter and a stent graft comprising a stent and a graft; delivering the catheter system to an area of interest in the blood vessel; and expanding the stent graft in the blood vessel. In some embodiments, a diameter of the stent graft expands about 4.5, 5.5, 6.3, 7.1, 7.7, 8.4, 8.9, 9.5, or 9.7 times or more and about 17.3, 15.8, 14.1, 12.2, 11.8, 11.4, 11.0, 10.5, 10.0, 9.5, 8.9, 8.4, 7.7, or 7.1 times or less compared to the diameter of the stent graft in the catheter prior to the expansion. In additional embodiments, a volume of the stent graft expands about 20, 30, 40, 50, 60, 70, 80, 90 or 95 times or more and about 300, 250, 200, 150, 140, 130, 120, 110, 100, 90, 80, 70, 60 or 50 times or less compared to the volume of the stent graft in the catheter prior to the expansion. The volume of a stent graft is calculated by the following equation:

$$V=\{(\text{inner diameter (ID) or outer diameter (OD)})/2\}^2 \pi \times \text{length of grate}$$

In one aspect, the vascular disease is aortic aneurysm, and the area of interest is an area of aneurysm. In additional embodiments, the vascular disease is selected from the group consisting of abdominal aortic aneurysm and thoracic aortic aneurysm. In further embodiments, the catheter is about 18, 17, 16, 15, 14, 13, 12, 11, 10, 9, 8, 7, or 6 French (Fr) or less and/or about 4, 5, 6, 7, 8, 9, 10, 11, 12, 13, 14, 15, 16, 17 or more. The Fr is a measure of the external diameter of the catheter, and, for example, a round catheter of 6 Fr has an external diameter of 2 mm. In some embodiments, the subject has an aortic vessel having an inner diameter of about 9, 8, 7, 6, 5, 4, 3 mm or less and about 1, 2, 3, 4, 5 or 6 mm or more. In further embodiments, the subject is Asian. In additional embodiments, the subject has a damaged or weakened blood vessel. In yet additional embodiments, the subject has diabetes mellitus.

As used herein, the term "about" modifying, for example, the quantity of an ingredient in a composition, concentrations, volumes, process temperature, process time, yields, flow rates, pressures, diameters, lengths, and like values, and ranges thereof, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

In another aspect, the methods described herein further comprise preparing the catheter system by inserting a stent graft system into a catheter. In some embodiments, the stent graft system comprises a stent, a graft, a suture, and a guide wire. In additional embodiments, a stent graft comprises a proximal end, a distal end, and a lumen disposed between the proximal end and the distal end, wherein the stent graft comprises a graft and a stent joined together with a suture thread(s).

In another aspect, the graft may be a woven fabric having an average thickness of about 10, 11, 12, 13, 14, 15, 20, 25, 30, 35, 40, 45, 50, 60, 70, 80, 100, 150, 200, 250, 300 μm or larger and 350, 300, 250, 200, 150, 100, 90, 85, 80, 70, 60, 50, 40 or 30 μm or smaller. In some embodiments, the graft has a constant diameter within ±20, 15, 10 or 5%. In further embodiments, the average thickness of the graft described herein may be measured with a thickness gauge at a total of 12 positions involving four roughly equally spaced positions in the circumferential direction of the graft measured three times in the length direction (e.g., 10 cm to 30 cm). In further embodiments, the graft comprises a woven fabric comprising at least one material selected from the group consisting of polyester including, but not limited to, poly(ethylene terephthalate), polylactide, polyglycolide and copolymers thereof, polyamide, polyolefin, polytetrafluoroethylene, and silk. The graft of the some embodiment may comprise a monofilament or a multifilament.

In yet additional embodiments, the graft comprises at least about 20, 30, 40, 50, 60, 70, 80, 90 or 95 wt % or 100 wt % of a polyester fiber. In further embodiments, the graft comprises a polyester fiber having about 98, 99 wt % or greater or 100 wt % polyethylene terephthalate component. In yet further embodiments, the graft satisfies one, three or four of the following conditions: (1) a reduced viscosity (ηsp/c) of about 0.80, 0.90, or 0.95 dl/g or greater, (2) a total fineness of between about 7, 8, 9, 10, 20, 30, 40, 50, or 100 dtex and about 120, 110, 100, 90, 80, 70, or 60 dtex, inclusive, and a single filament fineness of about 0.5, 0.4, 0.3, 0.2, or 0.1 dtex or less, and (3) a toughness parameter X of about 2.0, 3.0 or 5.0 or greater as represented by the following formula: X=(tensile strength×tensile elongation)/(total fineness×single filament fineness); a tensile strength of 3.5, 4.5, 5.5 or 6.5 cN/dtex or greater; and a tensile elongation of about 12, 13, 15, 20 or 30% or greater. In yet further embodiments, the polyester fiber further satisfies the following conditions: (4) for each of 10 sampled fiber bundles, where 10 fiber bundles of 1 cm are sampled at equal spacing of 3 m in the yarn length direction, the interfilament variation $Y_{(1-10)}$ represented by the following formula is about 0.5, 0.4, 0.3 or 0.2 or less:

$$Y_{(1-10)}=\sqrt{\{(d_i-d_{av})^2/(n-1)\}}$$

wherein n is a number of filaments corresponding to at least 30% of the total number of filaments from each of 10 fiber bundles, the yarn diameter $d_i$ is the diameter of each yarn among n filaments corresponding to at least 30% of the total number of filaments from each of 10 fiber bundles, and $d_{av}$ is the average for n filaments.

In yet further embodiments, the graft may be a seamless fabric constituted by a polyester fiber having about 85, 86, 87, 88, 89, 90, 91, 92, 93, 94, 95, 96, 97, 98 or 99 wt % or more of polyethylene terephthalate with respect to the graft weight, and the polyester fiber has a total fineness of about 1, 2, 3, 4, 5, 6, 7, 8, 9, 10, 20, 30, 40, 50, 60, 70, 80, 90, 100 or 110 dtex or more and about 130, 120, 110, 100, 90, 80, 70, 60, 50, 40, 30, 20 or 10 dtex or less and a single filament fineness of about 1.1, 1.0, 0.9, 0.8, 0.7, 0.6, 0.5 dtex or less and about 0.1, 0.2, 0.3, 0.4, 0.5, 0.6, 0.7, 0.8 or 0.9 dtex or more.

In some embodiments, the woven structure of the graft described herein is not particularly limited and may be a plain weave structure or a twill weave structure. The cover factors of the warp yarn and the weft yarn of the graft are both about 700, 800, 900, 1000 or 1100 or more, and the sum of the cover factors of the warp yarn and the weft yarn may be from about 1500, 1600, 1700, 1800, 1900, 2000, 2100 or 2200 to 2000, 2100, 2200, 2300 or 2400. The cover factors are calculated according to the following expressions using woven densities measured on the basis of JIS L 1096 (2010) 8.6.1:

Warp yarn cover factor=(Warp yarn total fineness: dtex)$^{1/2}$×(Warp yarn woven density: the number of warps/2.54 cm)

Weft yarn cover factor=(Weft yarn total fineness: dtex)$^{1/2}$×(Weft yarn woven density: the number of wefts/2.54 cm)

In some embodiments, the graft is tubular and/or branched. In additional embodiments, the graft may be a tubular seamless fabric or may have a structure of a plane woven fabric sewn in a tubular form. In some embodiments, the fiber may contain or be coated with a drug or extracellular material (ECM).

In some embodiments, the graft has a flexural rigidity of not more than about 0.060, 0.050, 0.040, 0.030 or 0.020 gf·cm$^2$/cm measured by Kawabata evaluation system (KES).

In some embodiments, the graft and suture thread may also be characterized as disclosed in PCT/JP2016/051300 and PCT/JP2016/060734, which are herein incorporated by reference in their entirety.

In another aspect, the term "stent" means any device or structure that adds rigidity, expansion force or support to a stent graft. In some embodiments, a stent may be self-expanding, balloon expandable or may have both characteristics. A zigzag stent is a stent that has alternating struts and peaks (i.e., bends) and defines a generally cylindrical space. A "Gianturco Z stent" is a type of self-expanding zigzag stent. In additional embodiments, the stent comprises at least one material selected from the group consisting of shape memory alloys, superelastic metals or synthetic polymer materials.

In another aspect, from 40, 45, 50, 55, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90% to 40, 45, 50, 55, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90% of the total inner cavity of the catheter inserted into the blood vessel is empty and void. Void in a catheter (%) may be measured by the following formula: Void in a catheter (%)=(cathothic cross-sectional area (X)−Stent graft system cross-sectional area (Y))/cathothic cross-sectional area (X)× 100, in which the cathothic cross-sectional area (X) is an inner cross-sectional area of catheter, and the stent graft system cross-sectional area (Y) is the sum of a cross-sectional area of a graft (Y1) and a cross-sectional area of the remaining materials in the catheter, including a stent graft system, such as stent, suture and guide wire (Y2).

In another aspect, the stent and graft described herein may be attached by any means know, for example, including stitching. In additional embodiments, the stent and the graft are stitched with a suture thread. In some embodiments, the fiber size of the suture thread is about 500, 450, 400, 350, 300, or 250 μm or smaller, and 100, 150, 200, 250, 300, 350, or 400 μm or more. In additional embodiments, the suture thread comprises a multifilament comprising at least one material selected from the group consisting of polyester, polyamide, polyolefin, polytetrafluoroethylene, and silk. In yet additional embodiments, the suture thread is in a braid form in which 2, 3, 4, 5, 6, 7, 8, 9, or 10 or more and 11, 10, 9, 8, 7, 6, 5, 4 or 3 or less fiber bundles (yarns) each comprising a plurality of filaments are interlaced, and the braid has a braiding angle of about 2, 3, 4, 5, 6, 7, 8, 9, 10, 11, 12, 13, 14, 15, 20° or larger and about 35, 30, 29, 28, 27, 26, 25, 20 or 15° or smaller and a braiding density of 10, 11, 12, 13, 14, 15, 20, 25, 30 or 35 counts/cm or higher and 50, 45, 44, 43, 42, 41, 40, 39, 38, 37, 36, 35, 30, 25, 20 or 15 counts/cm or lower. In further embodiments, the fiber bundles are highly bulked yarns having a porosity of from about 1, 2, 3, 4, 4, 5, 6, 7, 8, 9, 10, 15, 20, 25, 30, 35, 40, 45 or 50% to 50, 60, 70, 65, 60, 55, 50, 45, 40, 35, 30, 25, 20, 15 or 10%. Fibroblasts may enter moderate spaces formed between the filaments of the suture thread, and are organized, thereby filling needle holes at suture sites while helping to exhibit an effect of reinforcing the suture sites in living tissues. In addition, the modulus of elasticity of a suture thread can also be controlled to within the range of the present invention. In yet further embodiments, the fiber bundles comprise polyester and have a total fineness of about 20, 25, 26, 27, 28, 29, 30, 31, 32, 33, 34, 35, 45, 55, 65, 75, 85, 95, 105, 115, 125 or 135 dtex or more and about 200, 190, 180, 170, 160, 150, 140, 130, 120, 110, 100, 90, 80, 70, 60, or 50 dtex or less and a single filament fineness of about 1.1, 1.0, 0.9, 0.8, 0.7, 0.6, 0.5 dtex or less and about 0.1, 0.2, 0.3, 0.4, 0.5, 0.6, 0.7, 0.8 or 0.9 dtex or more. In some embodiments, when the suture thread inserted through the graft is pulled with a load of 60 g, the needle hole area of the graft is about 0.040, 0.030, 0.025, 0.020, 0.015, or 0.010 mm$^2$ or smaller.

In additional embodiments, the graft and suture thread may be those disclosed in U.S. Patent Application Publication Nos. 2015/0081004 and 2016/0184488, which are herein incorporated by reference in their entirety.

In some embodiments, the modulus of elasticity of the suture thread is about 50, 55, 54, 53, 52, 51, 50, 45, 40, 39, 38, 37, 36, 35, 34, 33, 32, 31, 30, 29, 28, 27, 26, 25 or 24 cN/dtex or less and about 1, 2, 3, 4, 5, 10, 20, 30, 31, 32, 33, 34, 35, 36, 37, 38, 39 or 40 cN/dtex or more. In the present specification, the modulus of elasticity of the suture thread that joins the graft and a stent together is an initial modulus of elasticity calculated from a load for 1% tensile elongation and a load for 2% elongation using data on load (also called stress) vs. elongation (also called strain) during pulling of the suture thread measured according to JIS-L-1013.

In another aspect, the method described herein further comprises sterilizing the stent grant prior to the insertion into the blood vessel. Methods for sterilizing medical equipment include heat sterilization methods such as autoclave sterilization using high pressure steam and dry heat sterilization using dry hot air, radiation sterilization methods using γ-ray or electronic beam, and gas sterilization methods using ethylene oxide gas or low temperature gas plasma of hydrogen peroxide. Sterilization methods or treatment conditions for medical equipment may be selected depending on the type and properties of matter to be sterilized, the state of storage in a container, etc. Similarly, a sterilization method or treatment conditions for the stent graft may be determined according to the properties of the stent, the graft, and other members, etc. Various physical properties described above, such as the modulus of elasticity, the braiding angle, and the braiding density of the suture thread, vary depending on the production histories of the suture thread, the method for finally sterilizing the stent graft, and its treatment conditions. For example, when the stent graft is produced using an unsterilized suture thread constituted by highly molecularly oriented polyester fiber bundles, and sterilized with dry hot air of 160 to 200° C., the modulus of elasticity of the suture thread, even if exceeding 40 cN/dtex before sterilization, may become 40 cN/dtex or less after the sterilization due to the thermal relaxation of the orientation. On the other hand, in the case of using the same polyester suture thread as above and adopting ethylene oxide gas sterilization, the treatment temperature may be about 60° C., which is lower than the glass transition temperature of the polyester fiber (e.g., 80 to 90° C.). Therefore, the modulus of elasticity of the suture thread does not become 40 cN/dtex or less after the sterilization. For attaining the object of the present invention (prevention of endoleak from needle holes after stent graft indwelling, and prevention of needle hole enlargement), the important thing is the physical properties of the suture thread in the finally sterilized sewn stent graft, not the physical properties of the suture thread used in the production of the stent graft.

The disclosure is also related to a catheter system comprising the catheter and the stent graft described herein in which a graft and a stent are connected with the suture, wherein a compression ratio of the stent graft is about 2.5%, 1.8%, 1.5%, 1.3%, 1.2%, 1.1% or less. In some embodiments, a filling factor of the stent graft in the catheter is from about 20, 21, 22, 23, 24, 25, 26, 2, 28, 29 or 30 to about 30, 31, 32, 33, 34, 35, 36, 37, 38, 39 or 40%. Compression ratio (%) may be measured by the following formula: Compression ratio (%)=inner volume of catheter (ID)/outer volume of stent graft after expansion (OD)×100 (=inner diameter (ID)$^2$/outer diameter (OD)$^2$×100).

EXAMPLES

A stent graft system including a stent, a graft, suture and a guide wire was inserted in a catheter. Compression ratio (%) was measured by calculating inner volume of catheter/outer volume of stent graft after expansion ((ID$^2$)/(OD$^2$))×100. Stent graft outer diameter (OD) after attaching a stent to outside or inside of a graft was measured outside of catheter in an expanded state. The stent graft outer diameter was measured on a straight scale with a minimum scale of 0.1 mm or less utilizing a magnifying glass (n=5; average value). The inner diameter of the catheter was measured with a caliper or a tapered conical gauge with a minimum scale of 0.1 mm or less (n=5; average value).

The catheter was cut at more than three sections along a diameter, and each cross-section was imaged. The inner cross-sectional area of catheter (X) was measured using a digital microscope SD measurement tool. Also, the digital microscope SD measurement tool was used to measure the cross-sectional area of the stent graft system other than the graft (Y2). The cross-sectional area of the graft (Y1) was calculated by the following formula: Y1=(OD/2)$^2$×π−[OD−2t)/2]$^2$×π). (i) An average thickness of the graft (t) was calculated from at least five positions on a circumference from an SEM image; and (ii) the outer diameter of stent graft in the catheter after expansion (OD) from the imaged cross-sections was measured using the digital microscope SD measurement tool discussed above.

The warp yarn and weft yarn shown in Table 1 were used to form a plain weave tubular seamless fabric for a graft with an inner diameter of 50 mm, using a shuttle weaving machine and a Jacquard opening apparatus. An average thickness of the fabric was measured using a thickness gauge with an IN load (n=5).

TABLE 1

| Polyester yarns used in Examples | | | |
|---|---|---|---|
| | Woven density | | Thickness |
| | Warp Density (no./inch) | Weft Density (no./inch) | of Woven fabric (μm) |
| PolyesterI | 203 | 137 | 69 |
| PolyesterII | 250 | 145 | 120 |
| PolyesterIII | 149 | 150 | 58 |

The woven fabrics were finished by scouring and heat setting. The woven density and the evaluation results for the obtained fabrics are shown below in Table 1.

Polyester fibers had no fluff and had satisfactory suitability for the textile processing steps, and the obtained fabrics were able to satisfy all of the target physical properties, including thickness, burst strength, and catheter insertability. Also, the variation in woven fabric thickness was in the range of ±2% to 10%, and therefore the thickness uniformity was excellent.

Eight W-shaped stent rings prepared with φ50 mm, the number of peaks of 4, the number of valleys of 4, and a height of 22 mm using a nitinol bar having a wire diameter of 0.5 mm were joined to the graft above (graft diameter: φ50 mm, length: 210 mm) by blanket stitching using the suture thread shown in Table 2 below. In this context, the suture needle used was a threaded suture needle (length: 14 mm, ½ circle) with each suture thread having a length of 1 m. The numbers of stitches at the peak section and the valley section were 4, the number of stitches per side was 12. The total number of stitches per structural unit was 160. The total number of stitches in the stent graft was 1280. The prepared stent graft was sterilized by an ordinary method using ethylene oxide gas.

As shown in Table 2, the modulus of elasticity of a suture thread is a tensile modulus of elasticity measured in a tensile tester TRAPEZIUM 2 (manufactured by Shimazu Corp.) according to JIS-L-1013, and was calculated from load for 1% tensile elongation and load for 2% elongation. To measure the braiding angle, braiding density, and fiber diameter of a suture thread, the suture thread was mounted onto an arbitrary stage without tension and observed under a microscope (digital microscope VHX-5000 manufactured by Keyence Corp.) at 200× magnification, and the braiding angle, braiding density, and diameter of the suture thread was determined using software included in the digital microscope. This operation was repeated five times in the length direction of the suture thread per m, and average values of the braiding angle, braiding density, and fiber diameter were calculated.

TABLE 2

| Physical properties of suture thread removed from sterilized stent graft | | | | |
|---|---|---|---|---|
| Material | Braiding angle (°) | Braiding density (counts/cm) | Fiber diameter (μm) | Modulus of elasticity (cN/dtex) |
| Polyester braid | 17 | 28 | 278 | 36.4 |

Characteristics of the exemplary catheter system are shown below in Table 3.

Based on the KES aesthetic property system, flexural rigidity measured using pure-bending testing machine KES-FB2 (made by KATO TECH Corp.). A 20 cm×20 cm specimen was grasped by 20 cm×1 cm of effective sample length under the environment of 20 degrees C.×65% RH, and curvature when bent under the conditions of ±2.5 (cm$^{-1}$) of maximum curvature measured the value which carried out division process of a changed part of the bending moment per unit width of ±0.5 to ±1.5-cm$^{-1}$ with curvature. The length of a textile and horizontal flexural rigidity were measured with the described method.

TABLE 3

Characteristics of the exemplary catheter system

|  | Example I | Comparative Example I | Example II |
|---|---|---|---|
| Graft used | PolyesterI | PolyesterII | PolyesterIII |
| Stent thickness (graft thickness) | 69 | 120 | 58 |
| Catheter size (OD) | 18 F | 18 F | 15 F |
| Catheter size (ID) | 17 F | 17 F | 14 F |
| Compressed volume/expanded volume (%) | 1.4 | 3.1 | 1.6 |
| Graft occupancy (%) | 19 | 24 | 24 |
| Void % in catheter | 67 | 62 | 65 |
| Flexural rigidity (gf·cm²/cm) | 0.014 | 0.084 | 0.016 |

The invention claimed is:

1. A method of treating a vascular disease in a subject in need thereof, comprising:
inserting a catheter system into a blood vessel of the subject, wherein
the catheter system comprises a catheter and a stent graft inside the catheter,
the stent graft comprises stent and graft, and
85 to 65% of the total inner cavity of the catheter is void;
delivering the catheter system to an area of interest in the blood vessel; and
expanding the stent graft in the blood vessel, wherein a compression ratio of the stent graft is 2.5% or less,
wherein the graft has 300 cc/cm²/min or less water permeability before and after needle puncture.

2. The method according to claim 1, wherein the vascular disease is aortic aneurysm or aortic dissection, and the area of interest is an area of aneurysm.

3. The method according to claim 1, wherein the vascular disease is selected from the group consisting of abdominal aortic aneurysm and thoracic aortic aneurysm.

4. The method according to claim 1, wherein the catheter is 15 French (Fr) or less, and the vascular disease is abdominal aortic aneurysm.

5. The method according to claim 1, wherein the catheter is 18 Fr or less, and the vascular disease is a thoracic aortic aneurysm.

6. The method according to claim 1, wherein the stent and the graft are stitched with a suture thread.

7. The method according to claim 1, wherein the stent comprises at least one material selected from the group consisting of shape memory alloys, superelastic metals or synthetic polymer materials.

8. The method according to claim 1, wherein the graft has a flexural rigidity of not more than 0.050 gf·cm²/cm measured by Kawabata evaluation system (KES).

9. The method according to claim 1, wherein the graft has a thickness of from 10 to 90 μm.

10. The method according to claim 1, wherein the graft comprises at least 20 wt % of a polyester fiber.

11. The method according to claim 1, wherein the graft comprises a polyester fiber having 98 wt % or greater polyethylene terephthalate component and satisfying the following conditions:
(1) a reduced viscosity (ηsp/c) of 0.80 dl/g or greater,
(2) a total fineness of between 7 dtex and 120 dtex, inclusive, and a single filament fineness of 0.5 dtex or less, and
(3) a toughness parameter X of 2.0 or greater as represented by the following formula: X=(tensile strength x tensile elongation)/(total fineness x single filament fineness);
a tensile strength of 3.5 cN/dtex or greater; and a tensile elongation of 12% or greater.

12. The method according to claim 11, wherein the polyester fiber further satisfies the following conditions:
(4) for each of 10 sampled fiber bundles, where 10 fiber bundles of 1 cm are sampled at equal spacing of 3 m in the yarn length direction, the interfilament variation $Y_{(1-10)}$ represented by the following formula is 0.5 or less:

$$Y_{(1-10)} = \sqrt{\{(d_i - d_{av})^2/(n-1)\}}$$

wherein n is a number of filaments corresponding to at least 30% of the total number of filaments from each of 10 fiber bundles, the yarn diameter $d_i$ is the diameter of each yarn among n filaments corresponding to at least 30% of the total number of filaments from each of 10 fiber bundles, and $d_{av}$ is the average for n filaments.

13. The method according to claim 1, wherein the graft is tubular and/or branched.

14. The method according to claim 1, wherein the subject is Asian.

15. The method according to claim 1, wherein the subject has diabetes mellitus.

16. The method according to claim 1, wherein 75 to 65% based on the total inner cavity of the catheter is void.

17. A catheter system comprising a catheter and a stent graft in which a graft and a stent are connected with a suture, wherein a filling factor of the stent graft in the catheter is 25 to 35%.

18. The catheter according to claim 17, wherein the catheter is 15 French (Fr) or less.

19. The catheter according to claim 17, wherein the catheter is 18 Fr or less.

20. The catheter according to claim 17, wherein the stent and the graft are stitched with a suture thread.

21. The catheter according to claim 17, wherein the stent comprises at least one material selected from the group consisting of shape memory alloys, superelastic metals or synthetic polymer materials.

22. The catheter according to claim 17, wherein the graft has a flexural rigidity of not more than 0.050 gf·cm²/cm measured by Kawabata evaluation system (KES).

23. The catheter according to claim 17, wherein the graft has a thickness of from 10 to 90 μm.

24. The catheter according to claim 17, wherein the graft comprises at least 20 wt % of a polyester fiber.

25. The catheter according to claim 17, wherein the graft comprises a polyester fiber having 98 wt % or greater polyethylene terephthalate component and satisfying the following conditions:
(1) a reduced viscosity (ηsp/c) of 0.80 dl/g or greater,
(2) a total fineness of between 7 dtex and 120 dtex, inclusive, and a single filament fineness of 0.5 dtex or less, and
(3) a toughness parameter X of 2.0 or greater as represented by the following formula: X=(tensile strength x tensile elongation)/(total fineness x single filament fineness);
a tensile strength of 3.5 cN/dtex or greater; and a tensile elongation of 12% or greater.

26. The catheter according to claim 25, wherein the polyester fiber further satisfies the following conditions:

(4) for each of 10 sampled fiber bundles, where 10 fiber bundles of 1 cm are sampled at equal spacing of 3 m in the yarn length direction, the interfilament variation $Y_{(1-10)}$ represented by the following formula is 0.5 or less:

$$Y_{(1-10)} = \sqrt{\{(d_i - d_{av})^2/(n-1)\}}$$

wherein n is a number of filaments corresponding to at least 30% of the total number of filaments from each of 10 fiber bundles, the yarn diameter $d_i$ is the diameter of each yarn among n filaments corresponding to at least 30% of the total number of filaments from each of 10 fiber bundles, and $d_{av}$ is the average for n filaments.

27. The catheter according to claim 17, wherein the graft is tubular and/or branched.

28. A method of treating a vascular disease in a subject in need thereof, comprising:

inserting a catheter system into a blood vessel of the subject, wherein the catheter system comprises a catheter and a stent graft inside the catheter, the stent graft comprises stent and graft, and 85 to 65% of total inner cavity of the catheter is void;

delivering the catheter system to an area of interest in the blood vessel; and expanding the stent graft in the blood vessel, wherein a compression ratio of the stent graft is 2.5% or less, wherein the graft has a thickness of from 10 to 90 μm.

\* \* \* \* \*